(12) United States Patent
Dobbe

(10) Patent No.: US 8,526,704 B2
(45) Date of Patent: Sep. 3, 2013

(54) MEASUREMENT OF FUNCTIONAL MICROCIRCULATORY GEOMETRY AND VELOCITY DISTRIBUTIONS USING AUTOMATED IMAGE ANALYSIS

(75) Inventor: Johannes Gijsbertus Gerardus Dobbe, Almere (NL)

(73) Assignee: Intellectual Property MVM B.V., Amsterdam (NL)

( * ) Notice: Subject to any disclaimer, the term of this patent is extended or adjusted under 35 U.S.C. 154(b) by 988 days.

(21) Appl. No.: 12/522,827

(22) PCT Filed: Jan. 10, 2008

(86) PCT No.: PCT/NL2008/050018
§ 371 (c)(1),
(2), (4) Date: Oct. 20, 2009

(87) PCT Pub. No.: WO2008/085048
PCT Pub. Date: Jul. 17, 2008

(65) Prior Publication Data
US 2010/0104168 A1    Apr. 29, 2010

Related U.S. Application Data

(60) Provisional application No. 60/879,808, filed on Jan. 11, 2007.

(30) Foreign Application Priority Data

Jan. 11, 2007  (EP) ..................... 07100408

(51) Int. Cl.
*G06K 9/62* (2006.01)
(52) U.S. Cl.
USPC ........................................ 382/134

(58) Field of Classification Search
USPC ......................... 382/128, 134, 300
See application file for complete search history.

(56) References Cited

U.S. PATENT DOCUMENTS

2005/0105786 A1*  5/2005  Moreau-Gobard et al. .. 382/128

OTHER PUBLICATIONS http://scholar.google.com/scholar_url?hl=en&q=http://citeseerx.ist.psu.edu/viewdoc/download%3Fdoi%3D10.1.1.137.48%26rep%3Drep1%26type%3Dpdf&sa=X&scisig=AAGBfm2l_fSH0QQwrxIE-hwBO_fd-97oww&oi=scholarr "An Auomated Method for Analysis of Flow Characteristic of Circulating Particles From In vivo Video Microscopy" Aug. 2005.*
International Search Report dated May 9, 2008.
Christopher G. Ellis et al., "Application of Image Analysis of Evaluation of Red Blood Cell Dynamics in Capillaries", Microvascular Research, 1992, pp. 214-225, vol. 44, No. 2, Academic Press, Inc., XP-008021694.
K. Haris et al., "Artery Skeleton Extraction Based on Consistent Curvature Labeling", Computers in Cardiology, 1999, pp. 269-272, IEEE, XP-010366995.
B. Jahne, "Image Sequence Analysis in Environmental and Live Sciences", 2003, pp. 608-617, Springer-Verlag, XP-007904617.

(Continued)

*Primary Examiner* — Robert Morgan
*Assistant Examiner* — Maroun Kanaan
(74) *Attorney, Agent, or Firm* — Young & Thompson

(57) ABSTRACT

The invention provides analysis algorithms for quantitative assessment of microvasculatory video sequences that provide vessel thickness, vessel length and blood velocity per vessel segment. It further provides a method of for calculating the functional microvasculatory density and blood velocity as distributed over vessels with different thickness, in the field of view.

16 Claims, 12 Drawing Sheets

(56) References Cited

OTHER PUBLICATIONS

T. Klyscz et al., "Cap Image—A Newly-developed Computer-aided Videoframe Analysis System for Dynamic Capillaroscopy", Biomedizinische Tecknik, 1997, pp. 168-175, vol. 42, No. 6, XP-001249359.

Nan Li et al., "Cortical Vascular Blood Flow Pattern by Laser Speckle Imaging", Proceedings of the 2005 IEEE, Sep. 1-4, 2005, pp. 3328-3331, IEEE, XP-010908520.

Michal Sofka et al., "Retinal Vessel Centerline Extraction Using Multiscale Matched Filters, Confidence and Edge Measures", IEEE Transaction on Medical Imaging, Dec. 2006, pp. 1531-1546, vol. 25, No. 12, IEEE, XP-002425428.

Anthony Sourice et al., "Red blood cell velocity estimation in microvessels using the spatiotemporal autocorrelation", Measurement Science and Technology, 2005, pp. 2229-2239, vol. 16, No. 11, IOP Publishing Ltd., XP-020090451.

\* cited by examiner

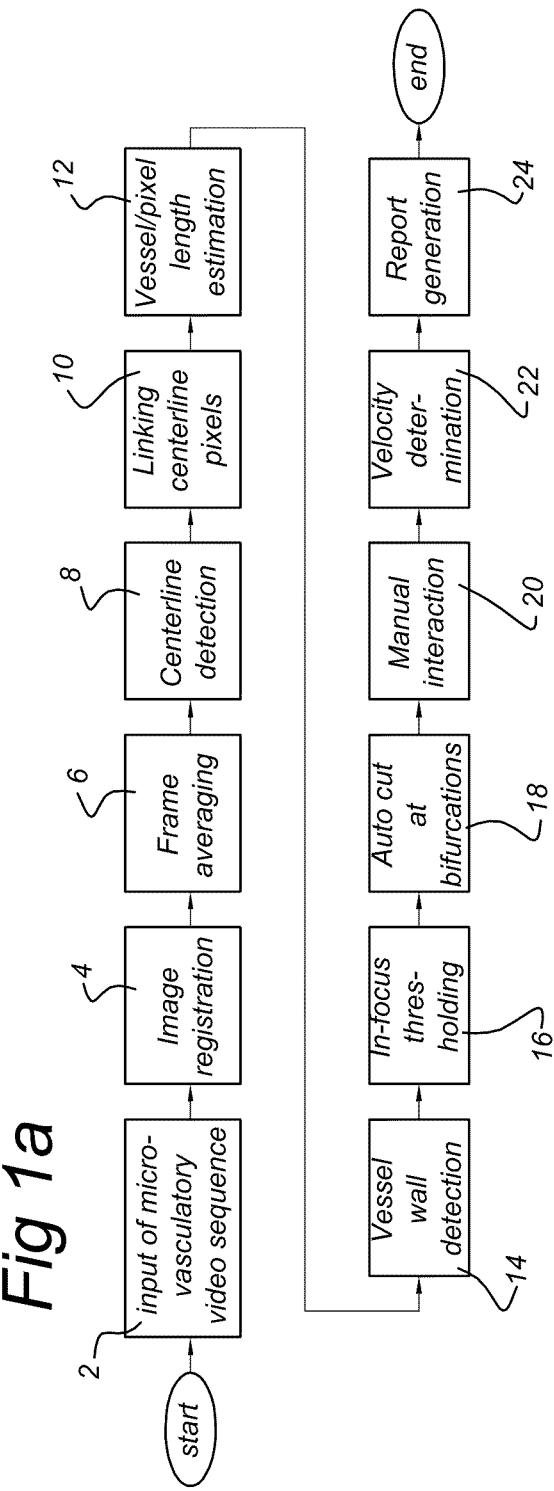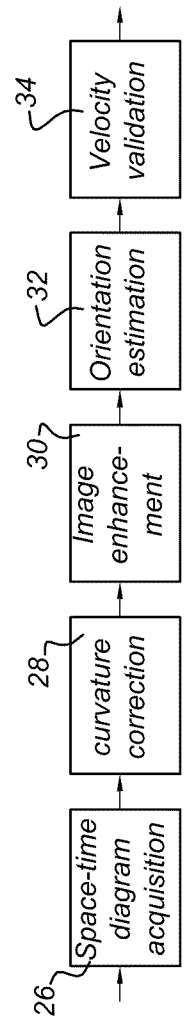

*Fig 2*
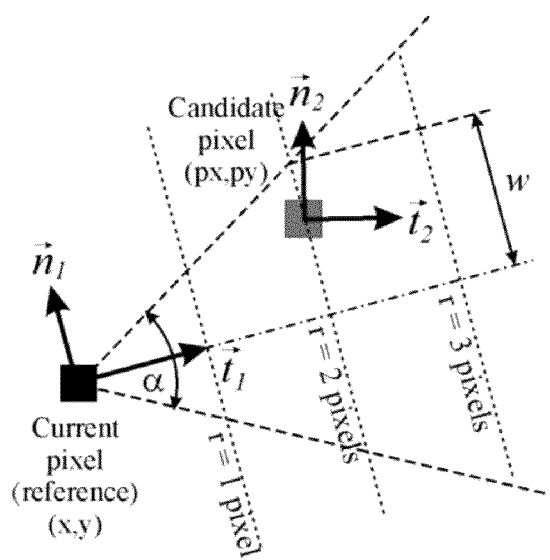
*Fig 3a*
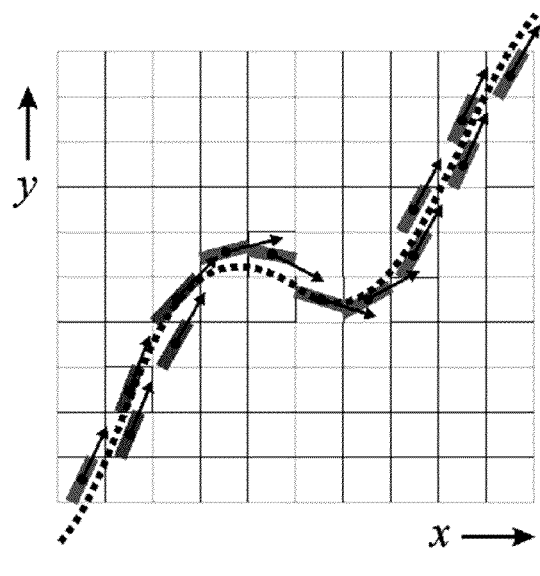
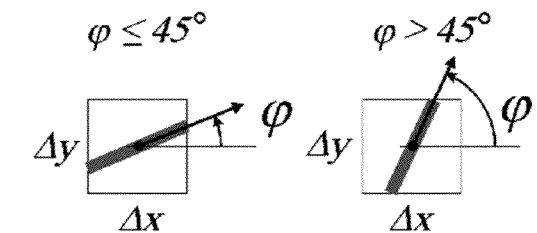
*Fig 3b*  *Fig 3c* a b c d

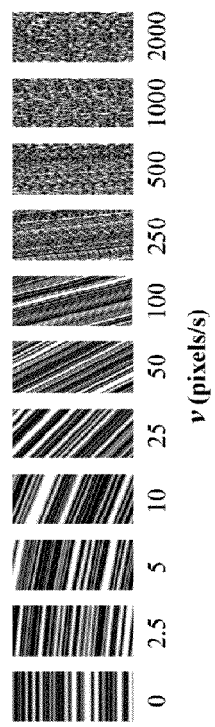
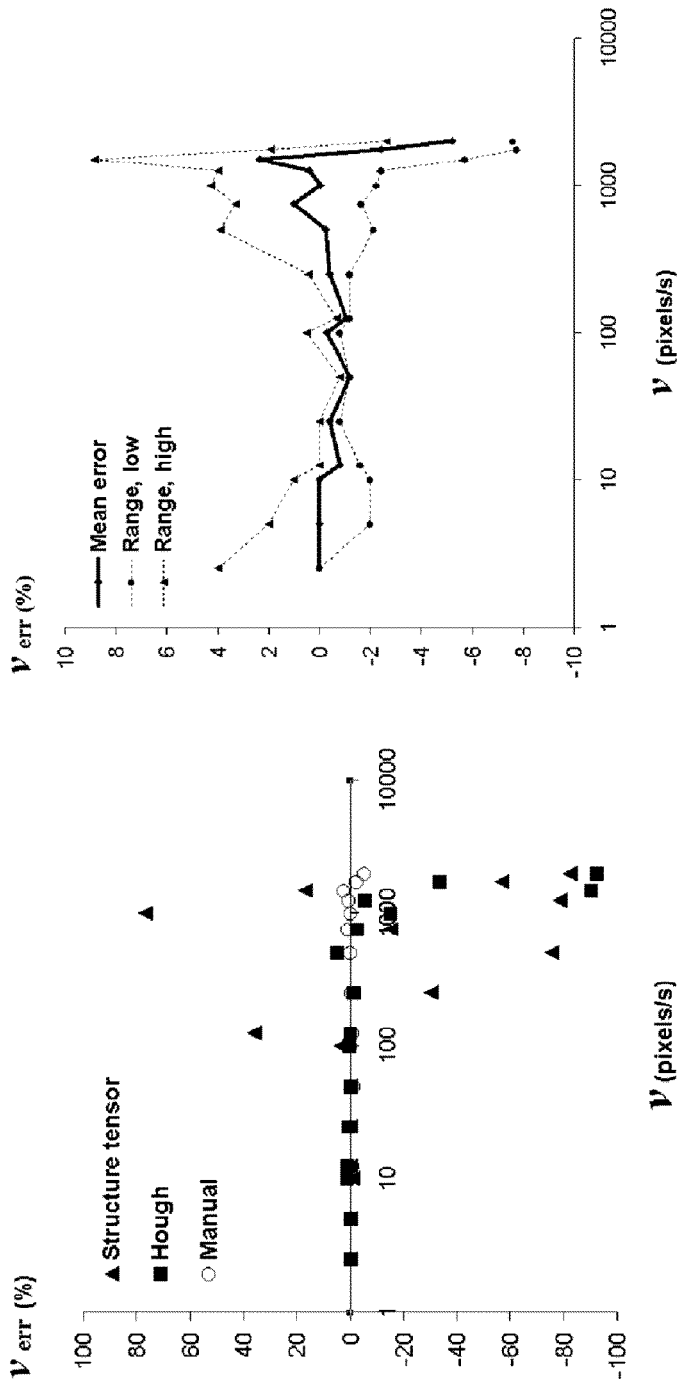
Fig 12a
Fig 12b
Fig 12c

*Fig 16a*  *Fig 16b*
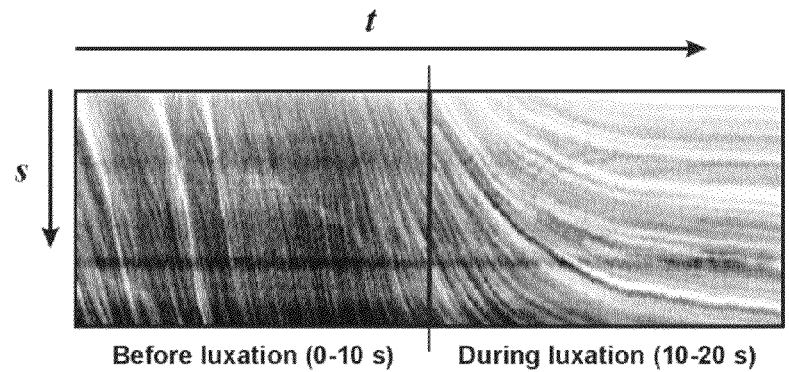
*Fig 17a*  *Fig 17b*
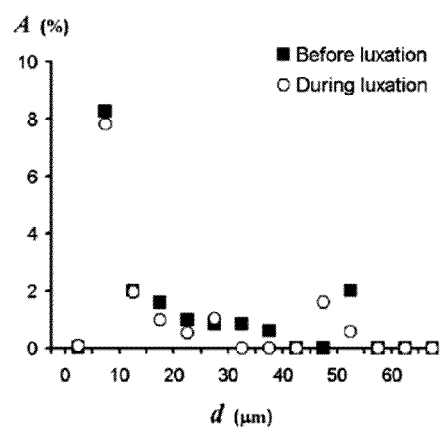 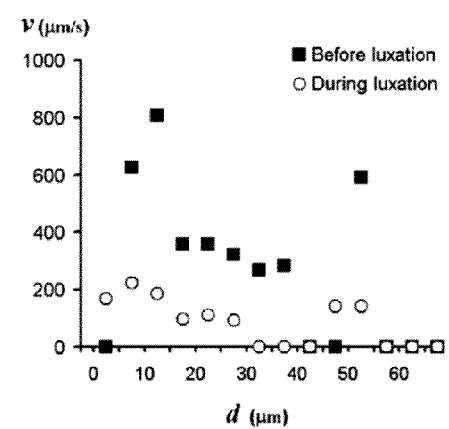

MEASUREMENT OF FUNCTIONAL MICROCIRCULATORY GEOMETRY AND VELOCITY DISTRIBUTIONS USING AUTOMATED IMAGE ANALYSIS

TECHNICAL FIELD

The present invention relates to a method of analyzing microvasculatory videos. It more particular relates to the measurement of functional microcirculatory geometry and blood velocity distributions.

BACKGROUND

Techniques for studying the human microcirculation in vivo have rapidly evolved in the last few decades. Capillaroscopy is a technique that uses an intravital microscope for imaging the microvascular bed. It has long been the only technique available to study the microcirculation of easy-accessible tissue, such as the skin or the capillary bed under the nail. The microscope-based configuration, however, makes capillaroscopy systems inaccessible to deep-lying tissue. More-recent studies describe the use of Orthogonal Polarization Spectral (OPS) imaging [3,4,18,20,23,25,30] or Side-stream Dark Field (SDF) imaging [13]. These techniques are basically hand-held microscopes with an advanced way of target illumination resulting in a higher contrast than is obtained with capillaroscopy systems [23]. Another big advance of these systems is the long probe, which makes the tip accessible to organ surfaces that cannot be reached with intravital microscopy. OPS-imaging systems have proved to be valuable in studying the microcirculation of, e.g., the human nail fold [23], sublingual tissue [20] during sepsis [30], brain tissue during aneurysm surgery [25], the colon in mice [3], skin flaps in mice [18] and in hamsters [10]. OPS studies are mainly observatory. Some OPS researchers used a semi-quantitative way of analysis where blood flow is scored [4,30] (no flow, intermittent flow, sluggish flow, continuous flow) in three vessel types: small (10-25 μm), medium (25-50 μm) and large (50-100 μm).

Besides quantitative geometry parameters for describing the microcirculation, there is increasing interest for quantification of microcirculatory blood velocity. Several methods have been described to determine velocity from a sequence of video frames [12,14,19,20]. Spatial correlation techniques [20] select a patch from a reference frame and trace that patch in subsequent frames. In the microcirculation, such patches undergo morphological changes. This is caused by the fact that cells near the vessel wall travel at a lower speed than cells at the center, and the fact that radial motion and motion perpendicular to the focal plane is also observed, e.g., due to vessel curvature. Optical flow techniques [12] rely on the fact that the intensity of traceable objects remains constant over time. Cells or clusters of cells also move in a direction perpendicular to the focal plane. This causes the intensity of objects to change in time as other cells overlap, which does not meet the continuous object intensity constraint. The use of anisotropic diffusion filters may overcome this problem yet require the existence of relatively large plasma gaps in order to detect large plugs of red blood cells.

The use of space-time diagrams for velocity estimation [14] has been used in many studies of the microcirculation [7,15,16,17,19,23,32]. These diagrams plot the longitudinal intensity profile of a straight vessel segment versus time. The diagonal bands in a space-time diagram represent objects traveling through the vessel. Bright bands are observed when a plasma gap or a white blood cell passes the vessel, while dark bands represent the presence of red blood cells. A big advantage of this technique is the fact that it includes all available space and time data for velocity estimation and the fact that the investigator receives immediate optical feedback of flow type from the lines that appear in the space-time diagram.

Klyscz and coworkers [17] described a computer program that features techniques for quantitative analysis of microvasculatory videos. Local vessel width is determined with an on-screen caliper; vessel length is obtained using a drawing tool that allows interactive tracing of vessels; it provides the functional capillary density (FCD), which is defined as the ratio of the total vessel length (L) (traced by the user) and the image area (A) of interest. It also estimates blood velocity using space-time diagrams [14,17,19]. Their method requires the user to draw a straight line at a vessel's centerline. The line indicates the location for acquiring image data to generate the space-time diagram. Although the program is unique in its field, it requires a large extent of user interaction, which increases observer bias and makes analysis time consuming.

SUMMARY OF THE INVENTION

An object of the present invention is to provide a method of analyzing microvasculatory videos for blood velocity determination, which requires less user interaction and reduces observer bias.

The object is realized by providing a method of analyzing microvasculatory videos for blood velocity determination, the method comprising:

receiving a sequence of microvasculatory video images, each of the video images showing a structure of vessels;

identifying vessel centerline pixels in the structure of vessels;

defining vessel segments by grouping the centerline pixels;

automatically producing a space-time diagram for each of the vessel segments, the space-time diagram being generated at the centerline pixels associated with each of the vessel segments;

automatically estimating a blood velocity in each of the vessel segments using the space-time diagram.

According to an aspect of the invention, there is provided a computer program product arranged to when being loaded on a computer, give the computer the capability to perform the method as described above.

According to a further aspect, there is provided a data carrier comprising such a computer program product.

BRIEF DESCRIPTION OF THE DRAWINGS

The present invention will be discussed in more detail below, using a number of exemplary embodiments, with reference to the attached drawings, in which:

FIGS. 1A and 1B show flow charts indicating processing steps according to an embodiment of the invention;

FIG. 2 shows a predefined capture area in which a next centerline pixel is sought;

FIG. 3A shows an imaginary line in an orthogonal pixel grid that describes the actual vessel centerline;

FIGS. 3B and 3C show two examples of a local vessel orientation $\phi$;

FIG. 12A shows eleven space-time diagrams at increasing velocity;

FIG. 12B shows a graph of an accuracy of velocity estimation using the structure tensor, gray-scale Hough transformation and interactive tracing of five lines in the space-time diagrams of FIG. 12A;

FIG. 12C shows a graph of a velocity error for interactive assessment in which the solid line represents the average velocity error and the dotted lines represent the accompanying velocity-error range;

FIG. 16 shows the space-time diagram of the venule marked by the arrow in FIG. 15A.

FIG. 17A shows a graph of a functional microcirculatory density distribution before and during luxation of the heart;

FIG. 17B shows a graph of a velocity distribution before and during luxation of the heart.

DETAILED DESCRIPTION OF EXEMPLARY EMBODIMENTS

Figure 4:
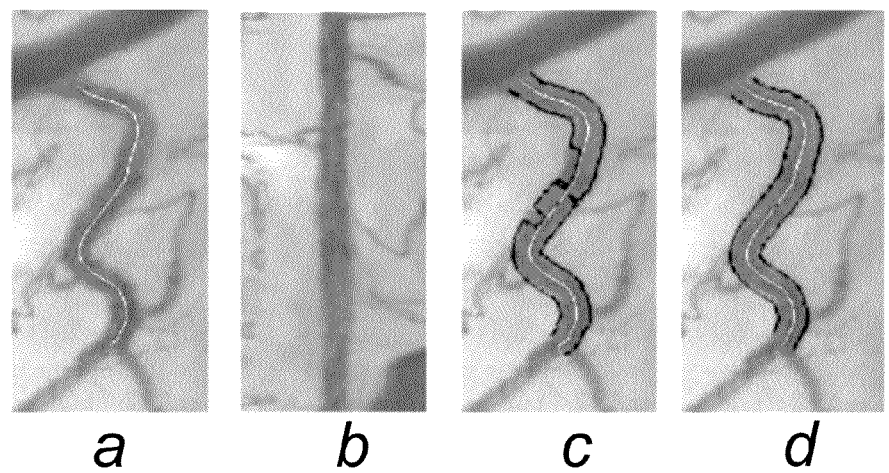
FIG. 4A shows an original vessel image.
FIG. 4B shows a straightened version of the vessel in FIG. 4A (centerline halfway each horizontal line)
FIG. 4C shows the centerline in the original image of FIG. 4A together with early results of vessel wall detection (showing locations where the vessel wall is misinterpreted)
FIG. 4D shows the result of filling gaps and smoothing the vessel wall.

With currently available imaging techniques, such as capillaroscopy, OPS or SDF imaging, "vessels" are only observed in the presence of red blood cells that contain hemoglobin, which highly absorbs the incident wavelength in contrast to the background medium. The capillary vessels themselves are basically invisible to these imaging techniques in the absence of red blood cells. Videos of the microcirculation merely show plugs of red blood cells that are delineated by the vessel wall and are therefore referred to as "vessels".

Vessel segmentation and blood velocity estimation using space-time diagrams requires many image processing steps. FIGS. 1A and 1B show flow charts indicating processing steps according to an embodiment of the invention. These processing steps can be executed by a computer arranged to perform one or more of the processing steps. In a first step 2, a microcirculatory video sequence is received from an imaging system. When making the video sequence, slight tip movements combined with the high effective optical magnification of hand-held micro vascular may result in inter-image translation. These inter-image translations hamper velocity measurements and are, according to an embodiment, compensated for by using 2D cross correlation, see Altman [2], in an image registration step 4. During the image registration step 4, image contrast may be enhanced in two ways; first, intensity variations in the background can be reduced for each frame by subtracting the quadratic polynomial surface that best-fits the image, and by adding the average image intensity of the original image; second, contrast improvement may be achieved by manipulating the image gray-scale histogram (8-bit range) by mapping each gray-level of the input image to a gray-level of the output image using a so-called transfer function, in a manner as described by Pries [26]. In a next step 6, video frames are time-averaged to fill up interruptions in capillaries that exist due to the presence of plasma gaps or white blood cells. Averaging causes capillaries to be detected as a whole, irrespective of interrupted cell flow. Averaging also reduces the contribution of noise, which is beneficial for the segmentation process. In a next step 8, the preprocessed image is subjected to centerline detection as described by Steger [31]. This method is based on calculating the eigenvectors of the Hessian matrix and results in a vector that points in the direction of the largest surface curvature [29] (i.e., perpendicular to vessel orientation) and a vector in the orthogonal direction, i.e., in the vessel direction. Image pixels are considered candidate centerline pixels if the surface curvature in the direction of n, represented by eigenvalue $\lambda_n$, is markedly higher than in the perpendicular direction t (tangent, along the vessel), represented by $\lambda_t$. This condition is tested by evaluating $|\lambda_n|/(|\lambda_n|+|\lambda_t|) \geq \epsilon_{thr}$, with $\epsilon_{thr}$ a given threshold value (Table 1). Candidate pixels are actually marked centerline pixels if the cross intensity profile, i.e., the intensity profile in the direction of n, is at its extremum [31].

Centerline detection results in a binary image in which centerline pixels are set to 1. In a step 10, these individual centerline pixels are linked into line segments for vessel length determination. This eases user interaction since "vessels" can be referred to instead of individual pixels. The vessel orientation influences the length contribution per pixel. This orientation resulted from Hessian analysis and is used in a step 12 to calculate the length contribution per pixel and the total length of a vessel segment that includes a number of pixels. In a next step 14, the vessel wall is detected for each centerline pixel and is marked by the points where the cross-intensity profile shows its maximum steepness. It provides estimates of the local vessel thickness and of the average vessel thickness.

If the microcirculation image is not in focus, the image appears blurred and causes an overestimation of vessel thickness in small vessels. Therefore, in a step 16, vessels that are out of focus are excluded. In an embodiment, the average gradient magnitude at all edge points of a vessel is used to determine a focus score F per vessel. This focus score is made less sensitive to background variations by normalizing it to the background intensity local (200×200 pixels$^2$) to each edge pixel. The focus score is defined as in [6]. In an embodiment, the user is enabled to include only vessels with a focus score that exceed a given limit.

Blood flow splits into new branches at a bifurcation, which causes blood velocity to change. For accurate blood velocity assessment, space-time diagrams need to be determined from pixels delineated by bifurcations. In a step 18, the process of cutting vessels at bifurcations is automated by determining the distance between a present vessel's ends and walls of neighboring vessels. If this distance is less than ¾× the neighbor's thickness, the neighbor is cut in two at the point closest to the present vessel's end. The ¾× factor (=1½× the neighbor's radius) allows cutting of vessel segments that approach the same junction, yet prevents cutting caused by nearby vessels, e.g., vessels that run parallel. The step 18 is performed for all available vessel segments.

In a step 20, a user is enabled to interact with these intermediate results by deleting, cutting, or concatenating vessel segments. Undetected vessel segments can be added "interactively" by local analysis at a selectable detection scale. A large scale of analysis focuses on large structural details, while a small scale focuses on small structures. Interactive analysis comprises the same analysis techniques as automatic analysis but at a selectable scale and in a local region identified by the user. The analysis region is based on the rectangle that bounds the end coordinates of a user-traced line. This region is slightly enlarged to detect an intended target vessel as a whole. Many vessel segments are usually found in such a rectangular region but only the one is selected that best fits the user-traced line. Next, for each vessel segment, a blood velocity is estimated, see step 22. The final results are displayed by a report generator that shows the vessel density and velocity distributions, see step 24.

Step 22 is explained in greater detail using FIG. 1B. FIG. 1B shows a flow chart of the steps to be taken in order to calculate the velocity in a vessel. The steps of FIG. 1B are repeated for each vessel segment in an area of interest. According to an embodiment, space-time diagrams are automatically acquired at each vessel's centerline, see step 26 in FIG. 1B. The space-time diagrams are corrected for vessel curvature, see step 28. In a step 30 image histogram equalization, see e.g. [27], is utilized to automatically improve visibility of the line structure in space-time diagrams.

Blood velocity is calculated by estimating an orientation of the lines in the space-time diagrams, see step 32. Nowadays, the orientation of the lines is estimated by interactively tracing lines in the space-time diagram or by using correlation techniques [17]. According to an embodiment of the present invention, the line orientation is calculated automatically by using a so-called structure tensor. In another embodiment, the estimation is done by using a gray-scale Hough transformation. The advantage of the automatic estimation is that no user interaction is needed for tracing lines in the space-time diagram during this step. In a next step 34 shown in FIG. 1B, the user may accept or reject the results of the automatic or interactive velocity analysis (validation). Finally, the orientation of the structure in the space-time diagram is converted to an actual velocity value in each of the respective vessel segments.

Some of the above described aspects are explained below in larger detail. The performance of the analysis algorithms described in this application depends on a large number of parameters that are listed in table 1.

Vessel Segmentation

Scale of Analysis

The centerline detection of step 8 described above requires determining image derivatives. These image derivatives are very noise sensitive if calculated as the difference between adjacent pixels. In an embodiment, Gaussian derivatives are therefore used that include image data within the working distance of the Gaussian kernel. The Gaussian counterparts of the above used derivatives are obtained by convolving the image with the corresponding derivative of a Gaussian:

$$I_i(x, y) = I(x, y) \otimes G_i(x, y) \tag{1a}$$
$$\{i = x, y\}$$

$$I_{i,j}(x, y) = I(x, y) \otimes G_{i,j}(x, y) \tag{1b}$$
$$\{i = x, y; j = x, y\}$$

$$G(x, y) = \frac{1}{2\pi\sigma^2} e^{-\frac{1}{2}\frac{x^2+y^2}{\sigma^2}}, \; G_i(x, y) = \frac{\partial G}{\partial i}, \; G_{i,j}(x, y) \frac{\partial^2 G}{\partial i \partial j} \tag{1c}$$

The standard deviation σ of the Gaussian filter serves as the scale parameter. Analyzing at larger values of the scale parameter increases the spatial scope of analysis and focuses on larger image features. The scale parameter σ is used for centerline detection. Other distance related analysis parameters are based on this scale parameter as indicated in table 1.

Grouping Centerline Points into Vessel Segments

The grouping of centerline pixels in step 10 requires linking pixels that are likely to belong to the same vessel segment. Pixels that exist due to noise or pixels of vessels that intersect or run parallel, are assigned to other vessel segments. Hessian analysis provides the tangent t and normal vector n at each centerline pixel x, see [31].

The linking starts at a centerline pixel having the highest curvature (highest second derivative, $\lambda_n$). Since a vessel may expand at two sides of this pixel, a trace for neighboring pixels continues in two opposite directions (towards t and towards −t), the current pixel x as reference, the method searches for a next pixel p=($p_x$, $p_y$) inside a predefined capture area that is best described by a triangle, defined by an opening angle α, with bisector towards tangent vector t, and a perpendicular bisector (towards n) at a distance r in a given search range ($r_{max}$), as indicated in FIG. 2. Candidate pixels p are calculated using:

$$p = x + rt + in \tag{2a}$$
$$(i = 0, \pm 1, \pm 2, \ldots, \pm w; r = 1, 2, \ldots, r_{max})$$

$$w = r\tan\left(\frac{\alpha}{2}\right) \tag{2b}$$

Several conditions can be used to differentiate between centerline pixels that belong to the same or to other vessel segments [29,31]. Two of them are listed below:
1) Since the vessel centerline is not abruptly changing direction from one pixel to the other, the tangent vector t at the candidate pixel's location should be similar to that of the reference pixel (x). This condition is satisfied if the inner product (c1) of the two tangent vectors is high.
2) The candidate pixel should belong to the same vessel as the reference pixel and not to a vessel that runs parallel to it. This rendition is tested by evaluating the inner product (c2) of the reference pixel's tangent vector and the distance vector to the candidate pixel.

The candidate pixel nearest to the reference pixel (smallest r) and with the highest score of c1+c2, as in [31], is accepted as the next centerline pixel in the vessel segment. Missing pixels between the reference pixel and the best neighbor are obtained by linear interpolation. The above-described procedure is repeated for grouping all individual centerline pixels that still remain into other vessel segments.

Each centerline pixel gives its contribution to the total vessel-segment length. An advantageous property of the centerline detection procedure is the fact that it yields single responses to a line [31]. Centerline pixels may be the result of image noise, especially when detecting vessels on a small scale. Since vessel segments that exist due to the presence of noise are usually small, all segments with a limited length (of $s_{min}$) are removed.

Vessel-Length Estimation, See Step 12 of FIG. 1

Vessel orientation influences the length contribution of each pixel. The local vessel orientation is therefore included in finding an estimate of vessel length. FIG. 3A shows an imaginary line (dotted) in an orthogonal pixel grid. The dotted centerline is represented by pixels (squares) that best described the actual vessel centerline. The bold line segments show the length contribution per pixel, the sum of which make up the total vessel length. In FIG. 3B, two examples of a local orientation $\phi$ is drawn. The local orientation $\phi$ is derived from the tangent vector (t) that resulted from Hessian analysis [31]. With $\phi$ known it is possible to calculate the pixel-length contribution $\Delta l$. If the principle direction is in the x-direction, i.e. $\phi \leq 45°$, and $\Delta x$ equals the length contribution of one pixel in horizontal direction, then $\Delta l = \Delta x / \cos(\phi)$. Otherwise $\Delta l = \Delta y / \sin(\phi)$, with $\Delta y$, the length contribution of one pixel in the vertical direction.

Vessel Wall Detection

Now an example is discussed of finding the wall of a single vessel, with reference to FIGS. 4A, 4B, 4C and 4D. FIG. 4A shows an original vessel image. FIG. 4B shows the same image as FIG. 4A, but straightened by subsampling the image in the normal direction. The centerline is located halfway each horizontal image line. FIG. 4C superimposes the result of early vessel wall detection on the original image of FIG. 4A. FIG. 4D shows the final result of vessel detection.

Using the tangent vector t and normal vector n at each centerline pixel, the cross-sectional intensity profile can be determined by sampling the image at subpixel level (by linear interpolation) in the direction normal to the tangent vector t. This process is repeated for each centerline pixel to obtain straightened vessels (see example in FIG. 4B). Gaps may occur in these straightened vessels if plasma gaps or white blood cells interrupt the continuous flow of red blood cells. For this reason an anisotropic diffusion kernel is used [11] with a Gaussian response that largely extends in the vertical direction ($\sigma_{along}$) of FIG. 4B. It effectively closes the interruptions and detects vessels as a whole. Horizontally, the first derivative of a Gaussian filter kernel is used as a maximum gradient detector, with a small extent in the cross direction ($\sigma_{cross}$) to preserve well localized edge detection [5].

Convolution with the edge detection kernel may bias vessel thickness estimation, especially for small vessels. The filter's own pulse response shows its highest gradient (G"(x)=0) at $x=\pm\sigma_{cross}$. Vessels are therefore detected as being at least $2\sigma_{cross}$ pixels wide.

Edge points cannot be detected correctly at, e.g., bifurcations, in cases where a large plasma gap occurs, or when vessels temporarily travel out of the focal plane hereby reducing the contrast to noise ratio, see FIG. 4C. Edge points may also be misinterpreted when a vessel with a higher intensity gradient runs parallel, or when vessels partly overlap. Misinterpreted edge points (artifacts) largely deviate by their mean distance to the centerline. This property is used to remove artifacts iteratively by excluding the most-distant edge point that exceeds 2 standard deviations from the mean distance in each iteration pass. This process is repeated until all remaining distance samples are within two standard deviations from the mean distance. The resulting mean distance is assigned to all artifact locations. Finally, Gaussian filtering ($\sigma_{edge}$) is performed to smooth the edge-centerline distances from one vessel end to the other as shown by FIG. 4D. The above described procedure is repeated for the opposite vessel wall and yields estimates of the local and average vessel thickness.

Velocity Determination

Figure 5:
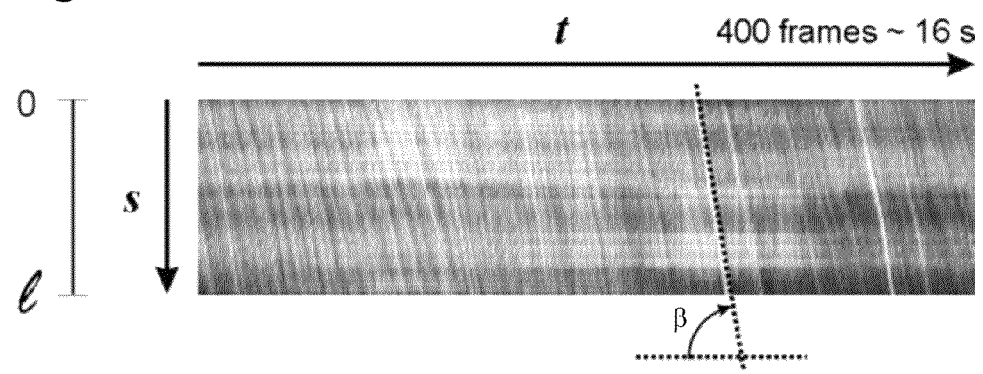
FIG. 5 shows an example of a space-time diagram.

In an embodiment, blood velocity in a vessel is estimated from the space-time diagram that is created automatically by plotting the centerline intensity versus time t as indicated in FIG. 5. The slope $\beta$ of the lines in a space-time diagram is a measure for blood velocity, which is calculated as: $v = \Delta s / \Delta t = \tan \beta$ with $\Delta s$ the displacement in time fragment $\Delta t$.

In contrast to blood flow in the smallest capillaries, the spatial velocity profile will be different in thicker vessels and may be similar to a Poiseuille parabolic flow where the velocity is at its maximum at the vessel centerline while zero at the vessel wall. In these vessel types, the velocity at or near the centerline is generally used as a velocity indicator [7,17,19, 20,23,32]. Nowadays, the orientation of the line structure is often estimated interactively, e.g., by tracing lines in the space-time diagram interactively and by calculating the average orientation. According to the invention, there is provided a method in which the orientation estimation of the lines in a space-time diagram is automatically determined.

Curvature Correction

Figure 6B:
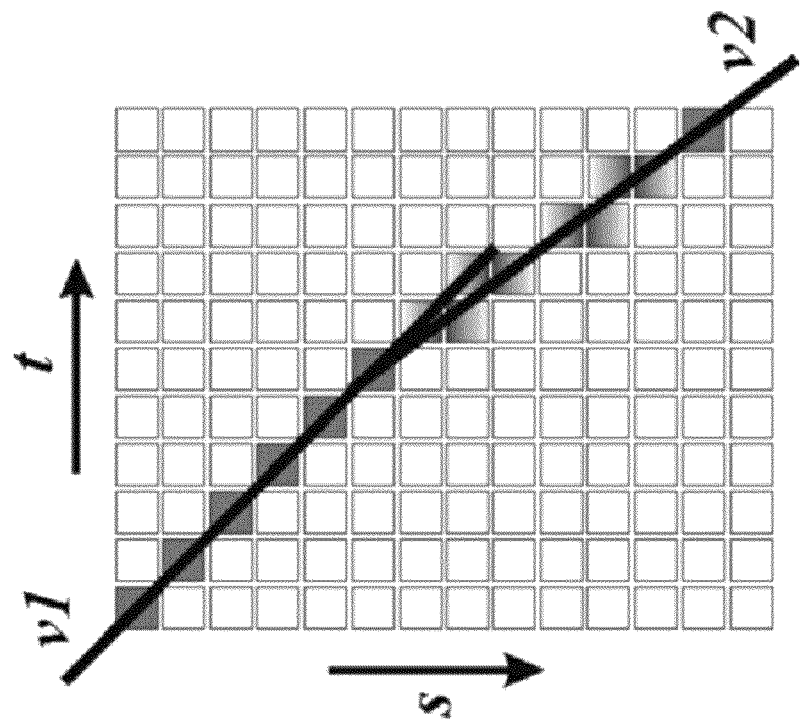
FIG. 6B shows a possible erroneous change of orientation in a space-time diagram (i.e., in velocity) due to a vessel orientation change.
Figure 6A:
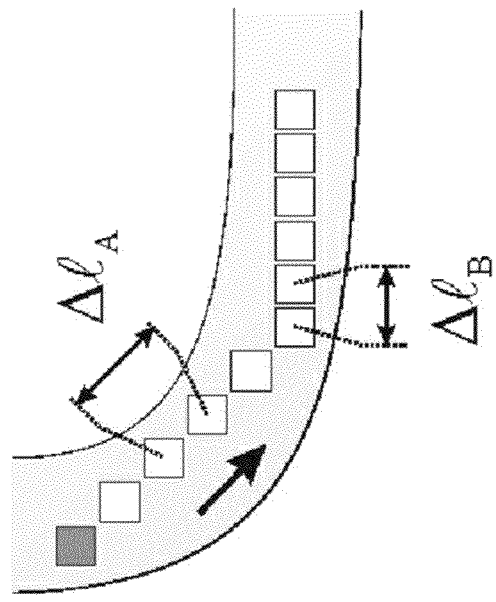
FIG. 6A shows an example of part of a centerline in a curved segment.

The time axis of space-time diagrams is a multiple of the frame interval, which is very accurate in CCD cameras. The space axis, on the other hand, is not uniformly distributed since the length contribution per pixel ($\Delta l_i$) depends on the local vessel orientation. This problem is illustrated in FIGS. 6A and 6B. If a dark object travels through a curved vessel (FIG. 6A) on a grid of pixels that is equally spaced in horizontal and vertical direction, the object passes the same number of pixels in the horizontal section ($\Delta l_B$), $\sqrt{2}$ times faster than the diagonal section ($\Delta l_A$). If the space-axis of the space-time diagram was simply a stack of centerline pixels, the velocity line would bend into a different direction when the vessel orientation changes (FIG. 6B), hereby falsely suggesting a change in velocity. This deflection error is avoided by mapping the randomly spaced centerline pixels onto the equidistant intervals of the space-time diagram using linear interpolation. In an embodiment, the number of distance samples is taken equal to the number of centerline pixels that describes a vessel.

Automatic Velocity Assessment Using the Structure Tensor

In an embodiment, the blood velocity is automatically calculated from the space-time diagram by estimation of the orientation of the lines using the structure tensor. Let $I(x)$ represent the 2D line-structure image, $x=(s,t)$. If $u=(\cos(\beta), \sin(\beta))^T$ is a unit vector pointing in the direction of the line structure, then $\beta(x+u) \sim I(x)$. In the direction perpendicular to u, i.e., in the gradient direction $\nabla I$, the intensity changes maximal. The direction of u is therefore found locally by solving:

$$u \cdot \nabla I = 0 \tag{3}$$

The average orientation may be estimated by minimizing E, the quadratic sum of deviations from Eq. 3, for all pixels in the space-time diagram using:

$$E = \sum_x \{I_t(x)\text{Cos}(\beta) + I_s(x)\text{Sin}(\beta)\}^2 \quad (4)$$

The optimal orientation is found by solving:

$$Ju = 0 \quad (5a)$$

$$J = \begin{bmatrix} \sum I_t^2 & \sum I_t I_s \\ \sum I_t I_s & \sum I_s^2 \end{bmatrix} \quad (5b)$$

with J the structure tensor containing Gaussian image derivatives (scale: $\sigma_{ST}$).

It can be shown, see also [14], that this minimization problem is equivalent to an eigenvalue problem: $Ju=\lambda\, u$. The eigenvector with the smallest eigenvalue yields the line orientation. The advantage of this approach is the fact that two eigenvalues result, that provide structural details. Suppose that $\lambda_t$ and $\lambda_n$ are the eigenvalues belonging to the eigenvectors in the line direction and in the normal direction. When lines appear in a single direction, then $\lambda_n>0$ and $\lambda_t\approx 0$. If multiple orientations are observed, then $\lambda_n>\lambda_t>0$ and, finally, if a dominant orientation is hardly found, $\lambda_n\approx\lambda_t\approx 0$. These properties are used to accept an automatic orientation estimation, and hence velocity estimation, if $|\lambda_n|/(|\lambda_n|+|\lambda_t|)>\mu_{thr}$.

Automatic Velocity Assessment Using Gray-Scale Hough Transformation

A space-time diagram sometimes shows small line artifacts with a different orientation compared to the global line structure. These are the result of intensity sampling at the vessel centerline using an orthogonal grid with a limited resolution. The small line artifacts can give a large contribution to the average line structure and do not focus on the interesting global Fine structure. Hough transformation [9], provides a way to include the length of lines in the space-time diagram and enables us to exclude small line artifacts. Hough transformation is basically a point-to-curve transformation that detects the parameters of straight lines in images. The technique considers the polar representation of a line:

$$\rho = x_i \text{Cos } \phi + y_i \text{Sin } \phi \quad (6)$$

With $(x_i, y_i)$ the coordinate of each line pixel in the space-time diagram, $\phi$ the orientation of the vector normal to the line and starting at the origin, and $\rho$ the length of this vector, which is equal to the line distance to the origin. Each line pixel is mapped to a sinusoidal curve in parameter space, $\rho(\phi)$. The discrete image of parameter space consists of accumulator cells, $H(\phi,\rho)$, that are incremented for each sinusoidal curve that passes the cell. By converting all line pixels of the space-time diagram into sinusoidal curves, the accumulator cells increment to the line length (L, in pixel units). An accumulator cell therefore yields the characteristic parameters $(\phi,\rho,L)$ of a line. With the space-time diagram as input image, a high response is expected at a specified orientation ($\phi$) and for multiple lines with a different distance to the origin ($\rho$).

Figure 7A:
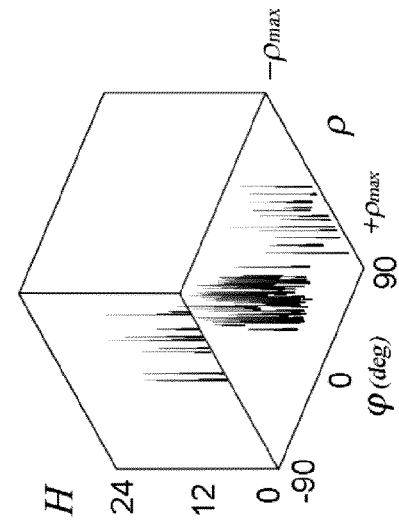
FIG. 7A is a graph of a Hough count as a function of φ and ρ derived at one gray level.
Figure 7B:
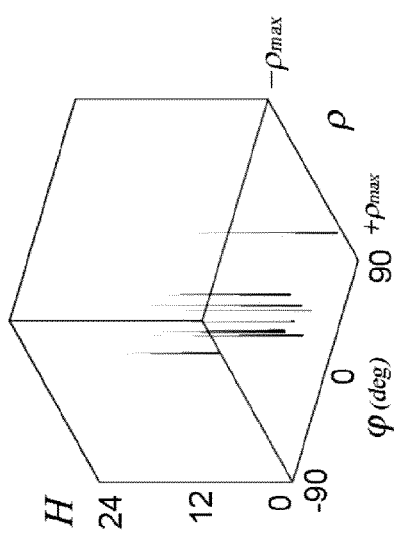
FIG. 7B is a graph of a Hough count for cells that are at least 90% of the largest value of FIG. 7A.
Figure 7C:
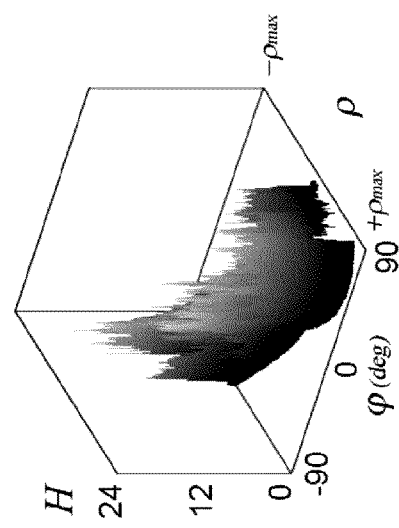
FIG. 7C is a graph that shows the sum of Hough counts as in FIG. 7B for all (or a selection of) gray levels.

The above-described conventional Hough transformation requires a binary image of the space-time diagram that may be obtained by, e.g., thresholding or line detection. Due to the limited image quality of space-time diagrams, these techniques poorly reveal the line structure and cause Hough transformation to give inaccurate results. More information is included by considering each gray level a binary image [21] (with pixels set to "1" if the gray level exists and "0" otherwise) that identifies its own set of lines, hence shows its characteristic peaks in Hough space. By repeating the Hough transformation for each gray level all pixels and gray levels are included in the transformation and are enabled to accumulate the responses. For each gray-level Hough transformation, see FIG. 7A, the accumulator cells that are at least 90% of the largest value are maintained while the others are set to zero. The result is shown in FIG. 7B. This includes only the longest lines per gray level and rejects small artifacts. These accumulator images "per gray level" are subsequently combined by summation and yield the "long-line" Hough space, see FIG. 7C.

Figure 8A:
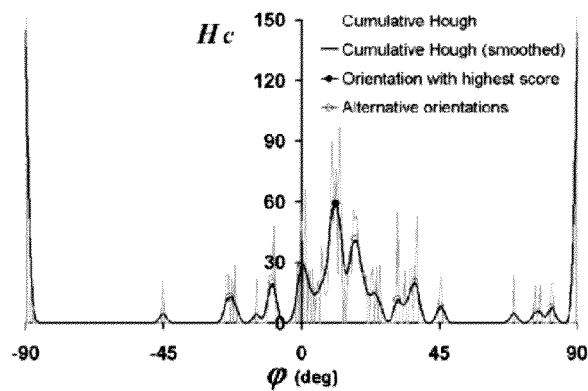
FIG. 8A is a graph of a Hough count as a function of φ.
Figure 8B:
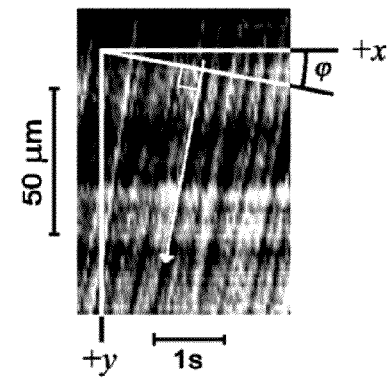
FIG. 8B is a corresponding space-time diagram showing the definition of φ.

Since only the global orientation is of interest, the total count of accumulator cells having the same orientation (but representing different line distances, $\rho$, to the origin) is determined, resulting in a "score" per orientation, see FIG. 8A. This curve is finally smoothed using a Gaussian filter kernel ($\sigma_H$). The highest peak in the filtered curve, representing a velocity in the range of velocity assessment (described below), gives the best estimation of the global line orientation, see FIG. 8B, and represents equally oriented long lines at different gray levels.

Range of Velocity Assessment

The physical upper limit of velocity assessment depends on vessel length (L in μm) and frame rate (f). Velocity measurements from slowly sampled scenes may be hampered by aliasing. It is theoretically possible to calculate blood velocity from the space-time diagram if an object travels at constant velocity and is visible in only two successive frames. However, it is not possible to tell with certainty whether the cell object in the first frame is the same as in the second frame. If one observes from additional video frames that the object moves with a rather constant displacement between successive frames, it is "more likely" that it is the same object. Therefore, a minimum of three frame intervals for determining the maximum physical velocity limit ($v_{max}$) is chosen:

$$v_{max} = \frac{L*f}{3} \; [\mu m/s] \quad (7)$$

Space-time diagrams are often marked by horizontal lines as a result of dark spots at fixed locations, e.g., due to intersecting vessels (see peaks at $\phi=\pm 90°$ in FIG. 8A), or by vertical lines, e.g., due to variations in illumination. Orientations that correspond to velocities above the physical limit, as described above, or below a given lower limit ($v_{min}$) are therefore rejected and require manual assessment, i.e., by tracing lines in the space-time diagram interactively.

Distributions

With vessel length, vessel diameter and blood velocity available it is possible to generate distributions that show 1) the contribution of vessel types in the field of view, and, 2) how blood velocity is distributed over vessels with different vessel diameter. If a vessel segment is considered to be a concatenation of centerline pixels, then each centerline pixel provides a contribution to vessel length, and provides a local vessel diameter. If all vessel segments are chained into one large imaginary vessel, this vessel would show a thickness variation that is given by the length-thickness distribution. It is obtained by subdividing the diameter contribution of each centerline pixel over the distribution bins, while using its length as weighting factor.

The area-thickness distribution (density distribution) is estimated in a similar manner. In this procedure vessel segments are subdivided into slices, one centerline pixel for each slice. The projection area of such slice is the product of the orientation dependent length and of local vessel diameter. The area-thickness distribution is determined by subdividing the diameter contribution of slices over the thickness bins while using the projection area as weighting factor.

The space-time method provides a measure of blood velocity per vessel that is assigned to each of its centerline pixels. The velocity-thickness distribution is determined by subdividing each slice thickness over the thickness bins while using the product of average velocity and the slice length as weighting factor.

Experiments

Validation

To validate the performance of vessel length and thickness determination, a simulation video (500×500 pixels) was created. Each frame contains five lines of different length (50, 100, 150, 200 and 250 pixels) with a Gaussian cross-sectional profile (with standard deviation $\sigma_l$). The "wall" of these simulated vessels is marked by the points where the maximum gradient is found, i.e., at $\pm\sigma_l$, yielding $d=2\sigma_l$, where d is the line thickness. Line thickness altered in consecutive frames, ranging [1, 20] pixels in 0.5-pixel increments. The background intensity and the centerline intensity were set to 200 au and 50 au (au=arbitrary units). Finally, Gaussian noise was added with $\sigma_{noise}=10$ au, which is approximately twice that of a typical SDF image. The effect of vessel orientation was studied by including frames with different line orientation in the range [0, 90]° with 15° increments.

Another simulation video (250×250 pixels) was created for validating velocity assessment. Each video frame shows a simulated vessel containing "cells" being circular blobs with a Gaussian cross-sectional intensity profile ($\sigma_{cell}=3$ pixels). These cells (approx. 1 cell per 5 pixels of vessel length, background intensity 200 au, center at 50 au) were drawn at random locations but within the boundaries of an imaginary vessel of 10 pixels wide that extends to the edges of each frame. The imaginary vessel wall is delimited by drawing blobs as close as $\sigma_{cell}$ from the vessel wall. Gaussian noise with amplitude 10 au was again added to the images. Perfusion was simulated by moving the cells out of the vessel while shifting in new cells in consecutive frames. The accuracy of interactive and automatic velocity assessment was tested in a vessel oriented at 0° in the velocity range [2.5, 2000] pixels/s (i.e., [0.1, 80] pixels/frame at 25 frames/s). Velocity results were first obtained by interactively tracing up to five available lines in the space-time diagrams. Interactively obtained velocity results served as reference for determining the error in automatic space-time diagram analysis using gray-scale Hough transformation and using the structure tensor method. A velocity error level up to 20% compared to interactive assessment was accepted during automatic analysis.

Rotational dependency was tested at a moderate velocity of 100 pixels/s by creating a comparable simulation video showing a vessel at different orientations in the range [0, 90]° with 15° increments. Velocity was determined interactively in this experiment.

Each velocity fragment covers 100 frames that were first averaged before segmentation and centerline detection. In the validation experiments the accuracy of assessment is given in pixels/s and is therefore irrespective of optical magnification.

Clinical Application

Sublingual video recordings were made using a MicroScan SDF system [13,22](MicroVision Medical, Amsterdam, The Netherlands) with a standard 5× optical magnification, which results in microcirculation images with a pixel spacing of approximately (h×v) 1.5×1.4 µm. This hardware features a point spread similar to a Gaussian distribution with a standard deviation <1.4 pixels in the x direction and <1.0 pixel in the y direction. Capillaries, having a diameter of about 4-5 µm, are therefore approximately 3-4 pixels wide in standard MicroScan images.

The sublingual microcirculation receives blood by lingual artery branching of the external carotid artery, which is part of the central body circulation. The sublingual video recordings of a healthy male individual was selected for its high contrast and moderate blood velocity, which allowed us to evaluate the feasibility of automatically analyzing space-time diagrams. The other sublingual recording was made during cardiac luxation in a patient who underwent cardiac bypass surgery using off-pump coronary artery grafting (OPCAB). The hemoglobin concentration and the hematocrit are not significantly changed during OPCAB surgery. During cardiac luxation the mean arterial pressure drops significantly (<60 mmHg). This video sequence was selected from a range of clinical experiments since it visualizes the microcirculation before and during the luxation procedure at practically the same sublingual location.

Analysis Parameters

The algorithms were configured for analysis of the evaluation and clinical image sequences using the settings given in table 1. Undetected vessel segments were added "interactively" by local analysis at a selectable scale (i.e., $\sigma=1.5, 3.0, 6.0$ or $12.0$ pixels).

TABLE 1

Parameter settings for automated microvascular analysis.

| Symbol | Description | Setting | Motivation |
| --- | --- | --- | --- |
| $S_{reg}$ | Range for searching reference patch in consecutive frames during registration | 25 pixels | Pragmatically determined. |
| $r_{max}$ | Search range for linking pixels | 5 pixels | Larger gaps chain spurious centerline pixels into long vessel segments. |
| $\alpha$ | Search angle for linking pixels | 90° | ±45° allows strong curvature yet rejects perpendicular continuation of a vessel. |
| $\sigma$ | Standard deviation of Gaussian derivatives for centerline detection; Many other filter segmentation parameters are derived from this scale parameter | 3 pixels | Pragmatically determined. |
| $\sigma_{cross}$ | Edge detection; standard deviation of highest derivative filter in direction normal to vessel orientation | $\frac{1}{3} \times \sigma$ | This filter gives no considerable overestimation of capillary thickness (>4 µm). |

TABLE 1-continued

Parameter settings for automated microvascular analysis.

| Symbol | Description | Setting | Motivation |
|---|---|---|---|
| $\sigma_{along}$ | Edge detection; standard deviation of averaging filter in vessel direction | $3 \times \sigma$ | This filter settings spans small plasma gaps. |
| R | Edge search distance | $20 \times \sigma$ | Pragmatically determined. |
| $S_{min}$ | Minimum vessel segment length | $5 \times \sigma^{(*)}$ | |
| $\sigma_{edge}$ | Standard deviation of edge distance smoothing | $3 \times \sigma$ | |
| $\epsilon_{thr}$ | Centerline detection threshold | $0.7^{(**)}$ | |
| $\mu_{thr}$ | Orientation detection threshold for space-time analysis | 0.6 | |
| $\sigma_{ST}$ | Standard deviation of space-time orientation detection using the structure tensor | 1.0 pixel | |
| $\sigma_H$ | Standard deviation for smoothing cumulative Hough diagram | 2° | |
| $v_{min}$ | Lower limit for velocity assessment | 2 µm/s | |

$^{(*)}$Set to $2 \times \sigma$ for interactive assessment
$^{(**)}$Set to 0 for interactive assessment

Validation Experiments

Vessel Length

Figure 9:
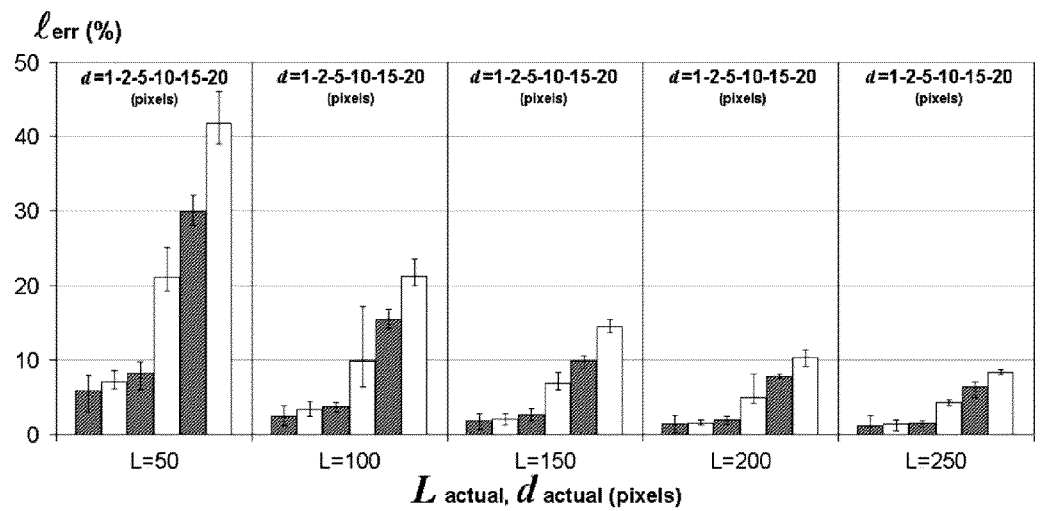
FIG. 9 shows an average length-estimated error for simulated vessels at different orientation, versus actual vessel length and width (in pixels). The error bars indicate the error caused by vessel orientation.

In two cases at d=1 pixel the vessel length was misinterpreted due to the presence of noise. In these particular cases the vessels were adjusted interactively. FIG. 9 shows the observed length deviation in pixel units. The bars depict the average length of determinations obtained at different orientations. The error bars indicate the small error range (<±2% on average) due to line orientation and noise. The graph shows that the accuracy of length assessment is irrespective of the line length but strongly depends on the thickness of the simulated vessel.

Figure 10:
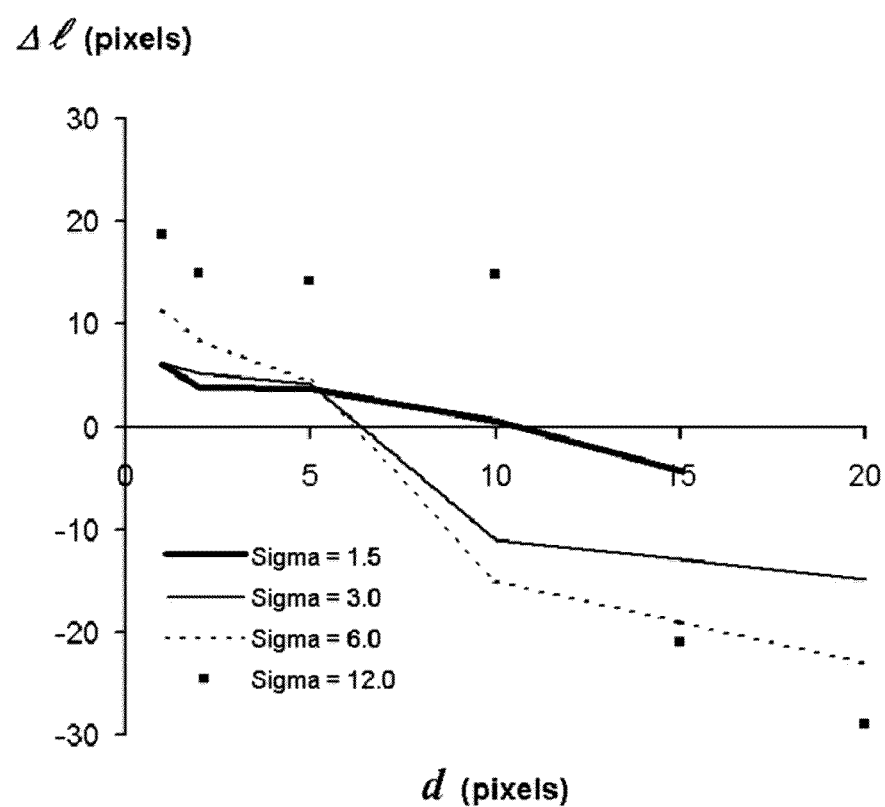
FIG. 10 shows the length estimation error for a simulated vessel with l=100 pixels at φ=0° and for different scales of analysis (sigma)

Length estimation also depends on the scale of analysis ($\sigma$) as can be seen in FIG. 10. This figure shows the length estimation error for a simulated vessel with l=100 pixels at $\phi=0°$. The figure demonstrates that misinterpretation of the vessel ends is limited when the scale of analysis is small ($\sigma=1.5$). At small scales however, detection is more sensitive to noise and a jagged vessel wall is detected for vessels wider than 12 pixels.

Vessel Thickness

The simulation video was also used for vessel thickness validation at four different scales (line detection scale $\sigma=1.5$, 3.0, 6.0, 12.0 pixels, i.e., $\sigma_{cross}=0.5$, 1.0, 2.0, 4.0 pixels). Vessel segments were selected interactively for this experiment. The "average" thickness served as thickness parameter. The effect of vessel orientation was again studied by including frames with different vessel orientation in the range [0, 90]° with 15° increments.

Figure 11A:
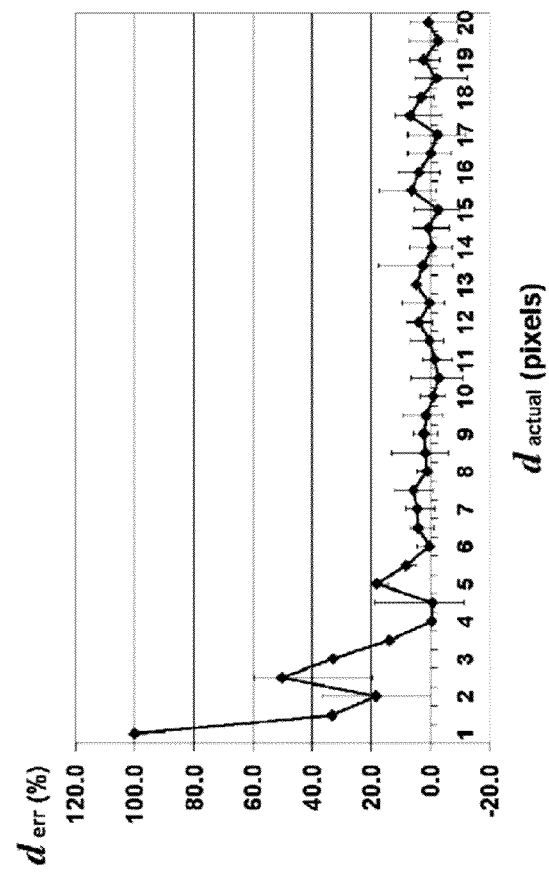
FIG. 11A shows a graph of a thickness estimation error (at scale, sigma=3.0) at different analysis scales.
Figure 11B:
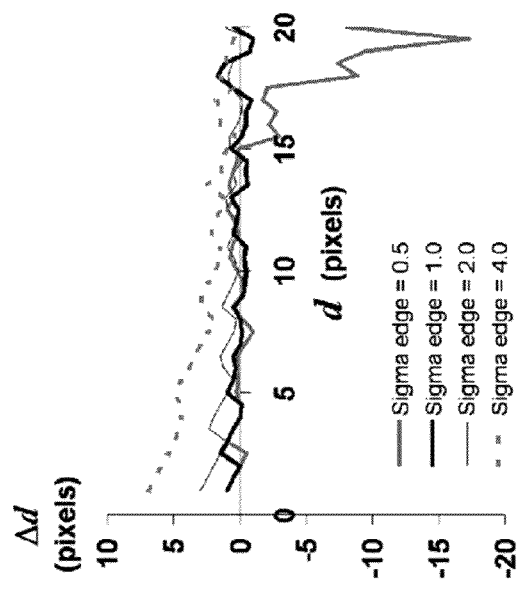
FIG. 11B shows a graph of an average thickness estimation error of simulated vessels at different orientations versus actual vessel thickness.

FIG. 11A shows that the thickness of small vessels is overestimated with increasing scale. This is caused by the filter's own pulse response that causes vessels to be detected as being $2\sigma_{cross}$ or wider, as discussed in "Vessel wall detection". It is therefore important to select a detection scale that is in agreement with the applicable vessel type. FIG. 11b further demonstrates the relative thickness-estimation error of simulated vessels when using the default analysis scale ($\sigma=3$) with an edge detection kernel $\sigma_{cross}=1$. The bars indicate the average thickness and the error bars indicate the range as a result of vessel orientation and noise. Vessels with a thickness in the range [$2\times\sigma_{cross}$, 13] pixels show an absolute thickness error of up to approximately 1 pixel, i.e., an error of 0.5 pixel in the detection of each wall. This small error results in a relative error that drops below 20% for vessels wider than 3 pixels (FIG. 11B).

Velocity

Blood velocity in the simulated video was estimated by interactive and automatic orientation estimation using the space-time diagrams shown in FIG. 12a. This figure shows that the line structure is clearly visible at low velocities while the images turn rather noisy at high velocities. Near the physical detection limit, which is approximately 2000 pixels/s in this experiment, the space-time diagrams barely reveal a line structure. However, line orientation can still be discovered by eye, for this simulation video, after some practicing. FIG. 12b shows the deviation in velocity assessment as obtained using three methods: 1) with the structure tensor, 2) using grayscale Hough transformation, 3) by tracing five lines in the space-time diagram interactively. Velocity assessment using the structure tensor works well for velocities up to 100 pixels/s (<5% accurate). Higher velocities are marked by local artifacts in the space-time diagram that result in large velocity errors (>20%). The method using Hough transformation performs excellent up to 750 pixels/s (<5% accurate). At higher velocities (>1250 pixels/s), the method fails and selects an alternative orientation that usually results in a large velocity error. Interactively tracing lines in the space-time diagram gives the best results and appears feasible up to the accepted physical velocity limit of 2000 pixels/s in this simulation experiment (accuracy <5%). FIG. 12C shows the average velocity error ($v_{err}$) and the velocity error range (dotted curves) as obtained by interactively tracing 5 arbitrary lines in the space-time diagram. It shows a rather small velocity error <4% for velocities up to 1000 pixels/s. Higher velocities show a larger error due to inaccuracy of tracing steep line segments. The influence of vessel rotation adds up to 1.1% to the error of velocity assessment for interactive and Hough determinations (not shown). Using the structure tensor the largest error due to rotation was 4.8%.

Clinical Application

Healthy Individual

Figure 13B:
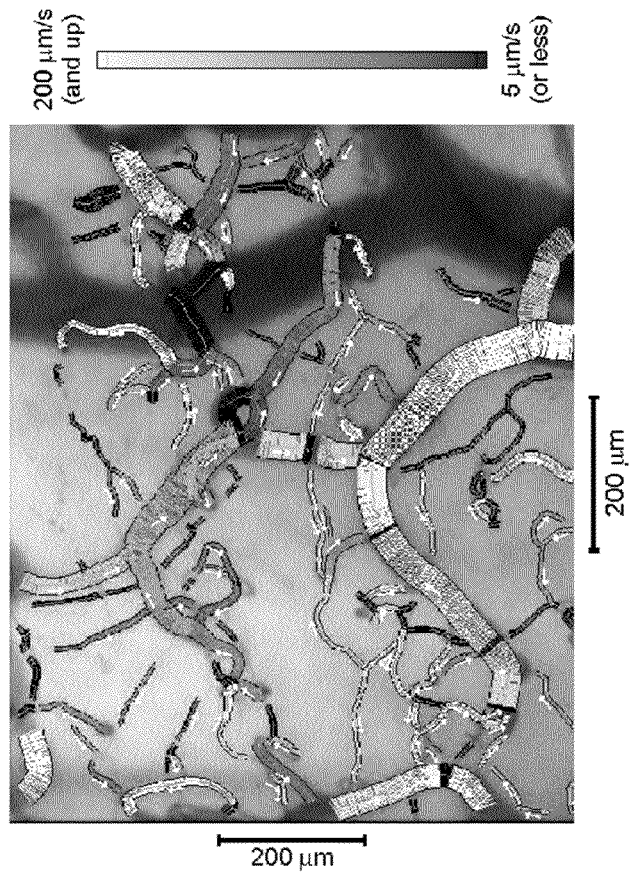
FIG. 13B shows the image of FIG. 13A with results of analysis superimposed.
Figure 13A:
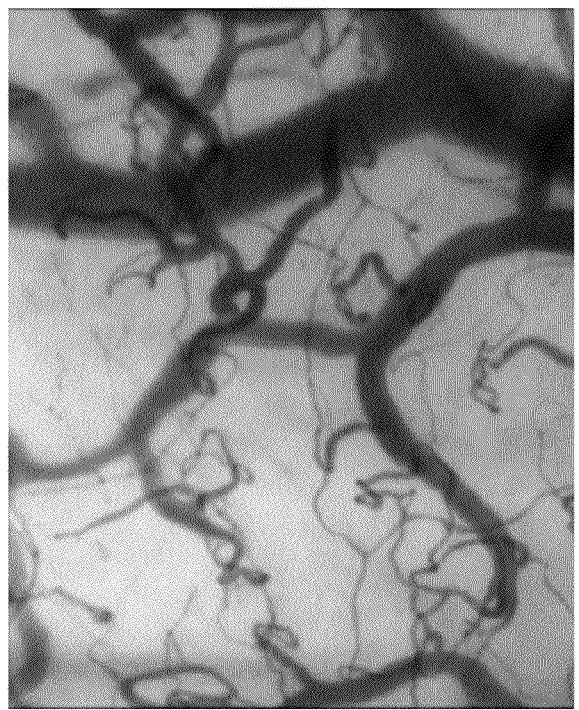
FIG. 13A shows an average frame of a sublingual video sequence of a healthy male individual.

The video recording of the healthy individual was analyzed after averaging frames within a 2 s interval, see image in FIG. 13a. The result of vessel segmentation is superimposed in FIG. 13b. In this experiment 31% of the total vessel length required manual interaction. The vessels in this image are color-coded and mark blood velocities in the range [5 (red), 650 (white)] µm. Vessel segments with space-time diagrams that could not be analyzed due to insufficient image contrast or with a line structure that represents a velocity above the physical limit (Eq. 7), are marked black. The thick vessel in the background was not segmented automatically because of the scale that was used for automatic detection.

Figure 14A:
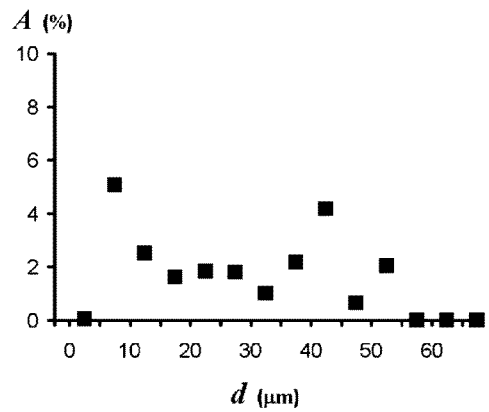
FIG. 14A shows a graph of a functional microcirculatory density distribution for a healthy male individual.

The functional microcirculatory density distribution is given in FIG. 14a. It shows that a large portion of the image area is occupied by capillaries in the range 5-10 μm.

Figure 14B:
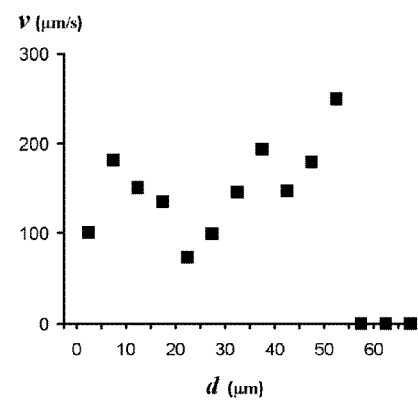
FIG. 14B shows a graph of a velocity distribution for a healthy male individual.

A total of 207 vessel segments were analyzed. In 99 (48%) segments the space-time diagrams did not reveal a visible line structure. In other cases vessel segments were too short to allow velocity analysis in the applicable range bounded by Eq. 7. The space-time diagrams of the remaining 108 (52%) vessel segments showed a line structure that was traced interactively. The velocity distribution in FIG. 14b illustrates that blood velocity is in the same order of magnitude in the given thickness range d<60 μm. Blood velocity was subsequently analyzed automatically in these 108 vessels. Using gray-scale Hough transformation, 29 segments (27%) fell within the 20% error level of acceptance. The tensor method analyzed 15 segments successfully (14%) in this experiment.

Cardiac Luxation

Figure 15A:
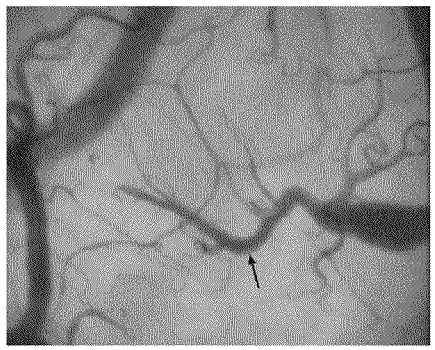
FIG. 15A shows an average frame out of a video sequence showing sublingual microcirculation before a luxation procedure.
Figure 15B:
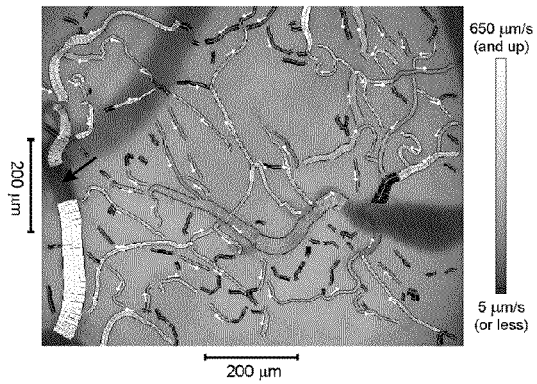
FIG. 15B shows the same image data as FIG. 15A but with results of analysis superimposed.
Figure 15C:
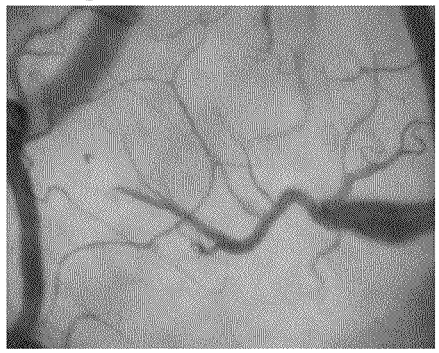
FIG. 15C shows an average of frames obtained during a luxation procedure.
Figure 15D:
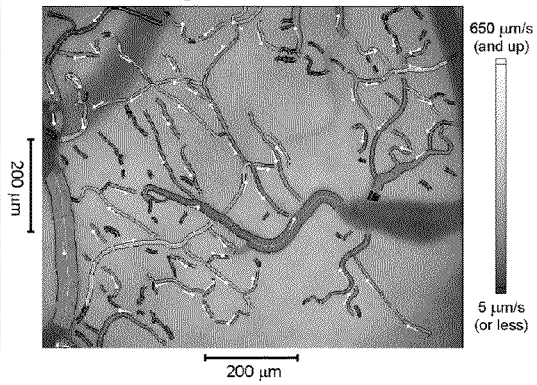
FIG. 15D shows analysis results superimposed on FIG. 15C.

FIG. 15A and FIG. 15C show the average of 250 frames (10 s) out of the sublingual video recording before and during cardiac luxation. The figures at the right (FIG. 15B and FIG. 15D) show the same video data with the results of analysis superimposed. In these two experiments 95% (before luxation) and 80% (during luxation) of the total vessel length was segmented automatically, the remaining vessels were added interactively FIG. 16 shows the spare-time diagram of the vessel marked by the arrow in FIG. 15A, and represents the interval before and during cardiac luxation. It clearly shows that blood velocity gradually reduces during luxation. Up to 20 lines were traced in each space-time diagram to get an impression of the average velocity during each 10 s interval. Space-time diagrams showed a clear line structure in 44% of the vessel segments before, and 48% of the vessel segments during luxation. These represent approximately 75% of the segmented vessel length in both cases. The vessels in FIG. 15B and FIG. 15d are again color-coded as in the previous experiment. It is clearly seen that blood velocity is reduced during cardiac luxation. FIG. 17B gives the velocity distribution, which shows that the average blood velocity is reduced to roughly one third of the original velocity in the whole thickness range.

The observed image area that was occupied by vessels in the cardiac luxation example changed from 17.1% to 14.6%, which is a 15% reduction. This finding is confirmed by exploring the images of FIG. 15. It shows that some small vessels are not visible, i.e. the presence of red blood cells is lacking or is reduced, during cardiac luxation. The shape of the density distributions is roughly the same (see FIG. 17A), as was expected, with an exception for vessels in the range 45-50 μm. This may be caused by a slight reduction of the observed red blood cells during luxation causing a reduction of the observed vessel thickness, and the discrete character of the distribution. Another source of error can be found in the segmentation of the single thick vessel that runs from the bottom-left upward with a thickness in the applicable range. This vessel is overlapped by another vessel with a higher contrast, which hampers segmentation of the thick vessel in FIG. 15b.

This invention provides advanced image analysis techniques that combine single-scale automatic analysis with interactive analysis on either of four selectable scales (e.g. σ=1.5, 3.0, 6.0, 12.0). The liberty of varying the scale for local vessel segmentation increases the detection range.

The length-validation experiments showed misinterpretations that are mainly due to the step-edge vessel ends that are not indicative for actual vessels and were not observed after analyzing actual microcirculation images. Considering the length of actual vessels (with an average length of approximately 100 pixels), the absolute length error of these simulated vessels yields rather small relative errors (<5% for capillaries up to 5 pixels wide). Length estimation further depends on centerline sensitivity parameter $\lambda_{thr}$. Reducing the threshold parameter increases line detection sensitivity and results in an overestimation of vessel length. This may be of advantage when vessels temporarily travel out of the focal plane. The experiments showed that length estimation is also influenced by the scale of analysis, the line detection threshold and by orientation. With the analysis scale set to σ=1.5 pixels, the simulated capillary vessel segment lengths (up to 15 pixels wide) were estimated to 5 pixels accurate. At this small scale of analysis, edge detection is largely influenced by image noise. For this reason it is better to analyze thicker vessels (>12 pixels wide) interactively at a higher scale of analysis. The fraction of thick vessels in a MicroScan image is relatively small (in terms of length) and therefore requires limited user interaction.

Line thickness was detected with an absolute error range of approximately ±1 pixel for vessels in the desired range of [1, 20] pixels wide. The effect of vessel orientation increases this error, especially for vessels wider than 13 pixels, with 1-2 pixels. This yields a relative thickness estimation error of less than 20% for vessels wider than 3 pixels as in standard MicroScan images. The liberty of selecting a scale for interactive analysis also introduces a disadvantage. Analyzing small vessels on a large scale, results in an overestimation of vessel thickness (FIG. 11a). On the other hand, analyzing thick vessels using the small-scale tool results in a jagged detection of the vessel centerline and its edges and yields an overestimation of vessel length. Visual inspection of the analysis results and operator understanding remains important for evaluating the results of analysis.

Interactive velocity estimation was quite accurate with an average velocity deviation of less that 4% in the range [0, 1000] μm/s. Vessel orientation adds 1% to this velocity error. The velocity error also depends on operator expertise and on the precision of tracing velocity lines. It is important to test the user contribution to this velocity error in future studies. Automatic analysis of space-time diagrams is preferential since it further reduces observer bias. Simulation videos showed that automatic analysis of space-time diagrams is feasible for velocities up to 750 pixels/s (±5%) using gray-scale Hough transformation. The structure tensor performed inferior to Hough detection, for velocities up to 100 pixels/s with similar accuracy (±5%). Automatic analysis of space-time diagrams obtained from clinical scenes will be successful if video recordings are rich in contrast, blood flow is rather constant (as is common for capillaries) and if there are sufficient plasma gaps to generate well-defined lines in the space-time diagrams. For future research it is recommended to further increase image contrast of existing SDF systems, which will improve automatic assessment of space-time diagrams. Pulsatile blood flow generates curved space-time diagrams that cannot be analyzed using the described gray-scale Hough method, since it relies on straight lines. The local scope of the structure tensor method yields an average measure of velocity and may be more suitable for these types of flow.

Blood velocities higher than $v_{max}$ (Eq. 7) cannot be detected using space-time diagrams. This range is especially limited in short vessel segments and at low video frame rates. Velocity detection will therefore benefit from high frame rates. This paper showed that velocity detection in clinical samples is feasible for video recordings with a high contrast, even using standard video frame rates (25 Hz) in sufficiently long vessel segments.

Until now, it has not been shown that the obstructive shock caused by cardiac luxation in patients is detrimental for adequate perfusion of the tissues. Using SDF imaging the direct effects of cardiac luxations on microvascular hemodynamics of the sublingual microcirculation is visualized and analyzed offline. During the episodes of shock with severe hypotension caused by cardiac luxations, the sublingual microcirculation perfusion was decreased to one third of the original blood velocity in the given experiment. The SDF video images showed some capillaries to fall out (no perfusion with erythrocytes) while others show a decrease in blood flow and some even show a complete stop of flow during cardiac luxations.

It can be concluded that the newly described vascular image analysis method described above, is a valuable tool that further reduces user interaction and observer bias and enables us in determining vascular parameter distributions that were otherwise impossible to obtain.

The present invention has been explained above with reference to a number of exemplary embodiments. As will be apparent to the person skilled in the art, various modifications and amendments can be made without departing from the scope of the present invention, as defined in the appended claims.

REFERENCES

1. Acton S T, Wethmar K, Ley K, "Automatic tracking of rolling leukocytes in vivo", Microvascular Research (2002), 63:139-148.
2. Altman D G, "Practical statistics for medical research", Chapman & Hall, USA 1999, ISBN: 0-412-27630-5, p 611.
3. Biberthaler P, Langer S, "Comparison of the new OPS imaging technique with intravital microscopy: Analysis of the colon microcirculation", European Surgery Research (2002), 24:124-128.
4. Boerma E C, Mathura K R, Van der Voort P H J, Spronk P E, Ince C, "Quantifying bedside-derived imaging of microcirculatory abnormalities in septic patients: a prospective validation study", Critical Care (2005), 9(6):R601-R606.
5. Canny J, "A computational approach to edge detection", IEEE Transactions on Pattern Analysis and Machine Intelligence (1986), PAMI-8(6):679-698.
6. Dobbe J G G, Streekstra G J, Hardeman M R, Ince C, Grimbergen C A, "Measurement of the distribution of red blood cell deformability using an automated rheoscope", Clincal Cytometry (2002), 50:313-325.
7. Ellis C G, Ellsworth M L, Pittman R N, Burgess W L, "Application of image analysis for evaluation of red blood cell dynamics in capillaries, Microvascular Research (1992), 44:214-225.
8. Geusebroek J M, "Robust autofocusing in microscopy", Cytometry (2000), 39:1-9.
9. Gonzalez R C, Woods R E, "Digital image processing", Addison-Wesley publishing company, Massachusetts 1992, ISBN: 0-201-50803-6.
10. Groner W, Winkelman J W, Harris A, Ince C, Bouma G J, Messmer K, Nadeau R G, "Orthogonal polarization spectral imaging: A new method for study of the microcirculation", Nature America (1999), 5(10): 1209-1213.
11. Ter Haar Romeny B M, "Front-end vision and multi-scale image analysis: Multi-scale computer vision theory and applications, written in Mathematica", Kluwer Academic Publishers, Dordrecht The Netherlands 2003, ISBN: 1-4020-1507-0, p 466.
12. Horn B K P, Schunck B G, "Determining optical flow", Artificial Intelligence (1981), 17:185-203.
13. Ince C, "The microcirculation is the motor of sepsis (review)", Critical Care (2005), 9(suppl 4): S13-S19.
14. Jähne B, "Digital image processing", $6^{th}$ revised and extended edition, ISBN 3-540-24035-7, Springer, Berlin Heidelberg New York, p 607.
15. Japee S A, Ellis C G, Pittman R N, "Flow visualization tools for image analysis of capillary networks", Microcirculation (2004), 11:39-54.
16. Japee S A, Pittman R N, Ellis C G, "A new video image analysis system to study red blood cell dynamics and oxygenation in capillary networks", Microcirculation (2005), 12:489-506,
17. Klyscz T, Ringer M, Jung F, Zeintl H, "Cap Image—ein neuartiges computerunterstütztes Videobildanalysesystem für die dynamische Kapillarmikroskopie", Biomedizinische Technik (1997), Band 42 Heft 6:168-175.
18. Langer S, Biberthaler P, Harris A G, Steinau H U, Messmer K, "In vivo monitoring of microvessels in skin flaps: Introduction of a novel technique", Microsurgery (2001), 21:317-324.
19. Lentner A, Berger F, Wienert V, "Das "Spatial Shift Alignment (SSA)" —eine neue Methode zur Bestimmung der Blutflussgeschwindigkeit in de Video-Kapillarmikroskopie", Biomedizinische Techniek (1994), Band 39 heft 7-8: 170-175.
20. Lindert J, Werner J, Redlin M, Kuppe H, Habazettl H, Pries A R, "OPS imaging op human microcirculation: a short technical report", journal of vascular research (2002), 39:368-372.
21. Lo R C, Tsai W H, "Gray-scale Hough transform for thick lline detection in gray-scale images", Pattern Recognition (1995), 28(5):647-661.
22. MicroVision Medical, Meibergdreef 45, 1105 BA Amsterdam, The Netherlands, www.microvisionmedical.nl.
23. Mathura K R, Vollebregt K C, Boer K, De Graaff J C, Ubbink D T, Ince C, "Comparison of OPS imaging and conventional capillary microscopy to study the human microcirculation", Journal of Applied Physiology (2001), 91:74-78.
24. Nolte D, Zeintl H, Steinbauer M, Pickelmann S, Messmer K, "Functional capillary density: an indicator of tissue perfusion?", International Journal of Microcirculation (1995), 15:244-249.
25. Pennings F A, Bouma G J, Ince C, "Direct observation of the human cerebral microcirculation during aneurysm surgery reveals increased arteriolar contractility", Stroke (2004), 35:1284-1288.
26. Pries A R, "A versatile video image analysis system for microcirculatory research", Int J Microcirc Clin Exp (1988), 7:327-345.
27. Russ J C, "The image processing handbook", $4^{th}$ edition, ISBN 0-8493-1142-X, CRC Press LLC, Florida (2002), p 732.
28. Slaaf, D W, Jeurens T J M, Tangelder G J, Reneman R S, Aarts T, "Methods to measure blood flow velocity of red blood cells in vivo at the microscopic level", Annual review of Biomedical Engineering (1986), 14(2):175-186.
29. Staal J, Abràmoff M D, Viergever M A, Van Ginneken B, "Ridge-based vessel segmentation in color images of the retina", IEEE Transactions on Medical Imaging (2004), 23(4):501-509.

30. Spronk P E, Ince C, Gardien M J, Mathura K R, Oudemans-Van straaten H M, Zandstra D F, "Nitroglycerin in septic shock after intravascular volume resuscitation", The lancet (2002), 360:1395-1396.
31. Steger C, "An unbiased detector of curvilinear structures", IEEE Transactions on pattern analysis and machine intelligence (1998), 20(2):113-125.
32. De Vriese A S, Verbeuren R J, Vallez M O, Lameire M H, De Buyzere M, Vanhoutte P M, "Off-line analysis of red blood cell velocity in renal arterioles", Journal of Vascular Research (2002), 37:26-31.

The invention claimed is:

1. A method of analyzing microvasculatory videos for blood velocity determination, said method comprising:
   a computer device receiving a sequence of microvasculatory video images from an imaging system, each of said video images showing a structure of vessels;
   the computer device identifying vessel centerline pixels in said structure of vessels;
   the computer device defining vessel segments by grouping said centerline pixels;
   the computer device automatically producing a space-time diagram for each of said vessel segments, said space-time diagram being generated at said centerline pixels associated with each of said vessel segments;
   the computer device automatically estimating a blood velocity in each of said vessel segments using said space-time diagram,
   wherein said blood velocity in each said vessel segment is estimated by:
   using the computer device, performing a gray-scale Hough transformation $H(\phi,\rho)$, of said space-time diagram of said vessel segment, where $\phi$ is an orientation normal to that of a 2D line structure in said space-time diagram and $\rho$ is a distance of a line in said space-time diagram to an origin of said space-time diagram;
   using the computer device, calculating a cumulative Hough diagram described by:

$$H(\varphi) = \sum_\rho H(\varphi, \rho);$$

the computer device smoothing said cumulative Hough diagram;
   the computer device disregarding parts of said cumulative Hough diagram that correspond to absolute blood velocities below a given threshold value $v_{min}$ and above $v_{max}=L \times f/3$, with L the length of said vessel segment and f a video frame rate;
   the computer device selecting a highest peak of said cumulative Hough diagram within an orientation range corresponding to velocities $\pm[v_{min}, v_{max}]$, as being a global line orientation; and
   the computer device converting said global line orientation into said blood velocity.

2. Method according to claim 1, wherein said vessel centerline pixels in said structure of vessels are identified by way of:
   the computer device performing time averaging a plurality of video images to render an average image;
   the computer device calculating a Hessian matrix for each image pixel in said average image using Gaussian image derivatives;
   the computer device calculating a first eigenvector of said Hessian matrix in a direction along said vessel segment, a second eigenvector perpendicular to said first eigenvector, and a corresponding first and second eigenvalue;
   the computer device selecting candidate centerline pixels, said candidate centerline pixels being those image pixels where said second eigenvalue is markedly higher than said first eigenvalue; and
   the computer device selecting actual centerline pixels out of said candidate centerline pixels, as those pixels where a cross intensity profile normal to the vessel direction is less than 0.5 pixels from its extremum.

3. Method according to claim 2, wherein said method comprises the computer device mapping randomly spaced centerline pixels onto equidistant space intervals of said space-time diagram using linear interpolation, so as to avoid a deflection error in space-time diagrams of curved vessel segments.

4. Method according to claim 2, wherein said blood velocity in a vessel segment is estimated by:
   the computer device performing a gray-scale Hough transformation $H(\phi,\rho)$, of said space-time diagram of said vessel segment, where $\phi$ is an orientation normal to that of a 2D line structure in said space-time diagram and $\rho$ a distance of a line in said space-time diagram to an origin of said space-time diagram;
   the computer device calculating a cumulative Hough diagram described by:

$$H(\varphi) = \sum_\rho H(\varphi, \rho);$$

the computer device smoothing said cumulative Hough diagram;
   the computer device disregarding parts of said cumulative Hough diagram that correspond to absolute blood velocities below a given threshold value $v_{min}$ and above $v_{max}=L \times f/3$, with L the length of said vessel segment and f a video frame rate; and
   the computer device selecting a highest peak of said cumulative Hough diagram within an orientation range corresponding to velocities $\pm[v_{min}, v_{max}]$, as being a global line orientation; converting said global line orientation into said blood velocity.

5. Method according to claim 2, wherein said blood velocity is estimated by the computer device solving the equations:

$$Ju = 0$$

$$J = \begin{bmatrix} \sum I_t^2 & \sum I_t I_s \\ \sum I_t I_s & \sum I_s^2 \end{bmatrix}$$

with
J the structure tensor,
$I_s$ the first order Gaussian image derivative to a position s of said space-time diagram I(s,t),
$I_t$ the first order Gaussian image derivative to time t of said space-time diagram I(s,t), $u=(Cos(\beta), Sin(\beta))^T$ a unit vector pointing in the direction of a 2D line-structure in said space-time diagram, where $\beta$ is the orientation of said 2D line-structure.

6. Method according to claim 2, wherein said method comprises:
   the computer device generating a velocity distribution using a vessel thickness and a blood velocity for each of said vessel segments, said velocity distribution showing the velocity of the blood over a vessel thickness range.

7. Method according to claim 2, wherein said method comprises the computer device time averaging of said video images to fill up interruptions in capillaries that exist due to the presence of plasma gaps or white blood cells.

8. Method according to claim 1, wherein said method comprises the computer device mapping randomly spaced centerline pixels onto equidistant space intervals of said space-time diagram using linear interpolation, so as to avoid a deflection error in space-time diagrams of curved vessel segments.

9. Method according to claim 8, wherein said blood velocity in a vessel segment is estimated by:
the computer device performing a gray-scale Hough transformation $H(\phi,\rho)$, of said space-time diagram of said vessel segment, where $\phi$ is an orientation normal to that of a 2D line structure in said space-time diagram and $\rho$ a distance of a line in said space-time diagram to an origin of said space-time diagram;
the computer device calculating a cumulative Hough diagram described by:

$$H(\varphi) = \sum_{\rho} H(\varphi, \rho);$$

the computer device smoothing said cumulative Hough diagram; disregarding parts of said cumulative Hough diagram that correspond to absolute blood velocities below a given threshold value $v_{min}$ and above $v_{max}=L \times f/3$, with L the length of said vessel segment and f a video frame rate;
the computer device selecting a highest peak of said cumulative Hough diagram within an orientation range corresponding to velocities $\pm[v_{min}, v_{max}]$, as being a global line orientation; and
the computer device converting said global line orientation into said blood velocity.

10. Method according to claim 1, wherein said method comprises:
the computer device generating a velocity distribution using a vessel thickness and a blood velocity for each of said vessel segments, said velocity distribution showing the velocity of the blood over a vessel thickness range.

11. Method according to claim 1, wherein said method comprises:
the computer device generating a first microvasculatory density distribution using a vessel segment thickness and a vessel segment length for each of said vessel segments, said microvasculatory density distribution showing the contribution of vessel categories.

12. Method according to claim 11, wherein said method comprises:
the computer device generating a second microvasculatory density distribution using a vessel segment thickness and a vessel segment area for each of said vessel segments, said microvasculatory density distribution showing the contribution of vessel categories.

13. Method according to claim 1, wherein said method comprises the computer device performing time averaging of said video images to fill up interruptions in capillaries that exist due to the presence of plasma gaps or white blood cells.

14. A method of analyzing microvasculatory videos for blood velocity determination, said method comprising:
a computer device receiving a sequence of microvasculatory video images, each of said video images showing a structure of vessels;
the computer device identifying vessel centerline pixels in said structure of vessels;
the computer device defining vessel segments by grouping said centerline pixels;
the computer device automatically producing a space-time diagram for each of said vessel segments, said space-time diagram being generated at said centerline pixels associated with each of said vessel segments;
the computer device automatically estimating a blood velocity in each of said vessel segments using said space-time diagram,
wherein said blood velocity is estimated by solving the equations:

$$Ju = 0$$

$$J = \begin{bmatrix} \sum I_t^2 & \sum I_t I_s \\ \sum I_t I_s & \sum I_s^2 \end{bmatrix}$$

with
J the structure tensor,
$I_s$ the first order Gaussian image derivative to a position s of said space-time diagram I(s,t),
$I_t$ the first order Gaussian image derivative to time t of said space-time diagram I(s,t), $u=(\text{Cos}(\beta), \text{Sin}(\beta))^T$ a unit vector pointing in the direction of a 2D line-structure in said space-time diagram, where $\beta$ is the orientation of said 2D line-structure.

15. A non-transitory computer readable medium having recorded thereon a computer program product arranged to be loaded on and executed by a computer, and causing the computer to perform the steps of:
receiving a sequence of microvasculatory video images from an imaging system, each of said video images showing a structure of vessels;
identifying vessel centerline pixels in said structure of vessels;
defining vessel segments by grouping said centerline pixels;
automatically producing a space-time diagram for each of said vessel segments, said space-time diagram being generated at said centerline pixels associated with each of said vessel segments;
automatically estimating a blood velocity in each of said vessel segments using said space-time diagram,
wherein said blood velocity in a vessel segment is estimated by:
performing a gray-scale Hough transformation $H(\phi,\rho)$, of said space-time diagram of said vessel segment, where $\phi$ is an orientation normal to that of a 2D line structure in said space-time diagram and $\rho$ a distance of a line in said space-time diagram to an origin of said space-time diagram;
calculating a cumulative Hough diagram described by:

$$H(\varphi) = \sum_{\rho} H(\varphi, \rho);$$

smoothing said cumulative Hough diagram;

disregarding parts of said cumulative Hough diagram that correspond to absolute blood velocities below a given threshold value vmin and above $v_{max}$=L×f/3, with L the length of said vessel segment and f a video frame rate;

selecting a highest peak of said cumulative Hough diagram within an orientation range corresponding to velocities ±[$v_{min}$, $v_{max}$] as being a global line orientation; and converting said global line orientation into said blood velocity.

16. A non-transitory computer readable medium having recorded thereon a computer program product arranged to be loaded on and executed by a computer, and causing said computer to perform the steps of:

using the computer device solving the equations:

$$Ju = 0$$

$$J = \begin{bmatrix} \sum I_t^2 & \sum I_t I_e \\ \sum I_t I_a & \sum I_a^2 \end{bmatrix}$$

with

J the structure tensor, $I_s$ the first order Gaussian image derivative to a position s of said space-time diagram I(s,t), $I_t$ the first order Gaussian image derivative to time t of said space-time diagram I(s,t), u=(Cos(β), Sin(β))$^T$ a unit vector pointing in the direction of a 2D line-structure in said spacetime diagram, where β is the orientation of said 2D line structure.

* * * * *

UNITED STATES PATENT AND TRADEMARK OFFICE
CERTIFICATE OF CORRECTION

PATENT NO. : 8,526,704 B2
APPLICATION NO. : 12/522827
DATED : September 3, 2013
INVENTOR(S) : Johannes Gijsbertus Gerardus Dobbe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1087 days.

Signed and Sealed this

Fifteenth Day of September, 2015

Michelle K. Lee
*Director of the United States Patent and Trademark Office*